United States Patent
Farazi

(10) Patent No.: US 7,381,188 B1
(45) Date of Patent: Jun. 3, 2008

(54) SYSTEM AND METHOD FOR PROCESSING AND STORING SIGNAL INFORMATION IN AN IMPLANTABLE CARDIAC DEVICE

(75) Inventor: Taraneh Ghaffari Farazi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 136 days.

(21) Appl. No.: 11/185,270

(22) Filed: Jul. 19, 2005

(51) Int. Cl.
*A61B 5/04* (2006.01)
(52) U.S. Cl. .................... 600/508; 600/509
(58) Field of Classification Search ............ 607/9; 600/508, 515, 516, 518
See application file for complete search history.

(56) References Cited

U.S. PATENT DOCUMENTS

| | | | |
|---|---|---|---|
| 4,616,333 A * | 10/1986 | Shimoni ............... | 708/813 |
| 5,215,098 A | 6/1993 | Steinhaus et al. ......... | 128/702 |
| 5,836,889 A * | 11/1998 | Wyborny et al. .......... | 600/509 |
| 7,139,674 B2 * | 11/2006 | Switlik et al. ............. | 702/179 |
| 2003/0083713 A1 * | 5/2003 | Palreddy et al. ............ | 607/28 |
| 2003/0204146 A1 | 10/2003 | Carlsson .................. | 600/515 |

* cited by examiner

*Primary Examiner*—Carl H. Layno
*Assistant Examiner*—Brian T Gedeon
(74) *Attorney, Agent, or Firm*—Steven M. Mitchell

(57) ABSTRACT

In an implantable cardiac device data is processed and stored to conserve storage space and computational resources thereby saving energy expended on these operations. The data being processed may be associated with signals with known and/or predictable patterns. A set of key elements are identified for the signal that allow the signal to be reconstructed without saving a complete time series of data for the signal.

11 Claims, 6 Drawing Sheets

SYSTEM AND METHOD FOR PROCESSING AND STORING SIGNAL INFORMATION IN AN IMPLANTABLE CARDIAC DEVICE

TECHNICAL FIELD

This application relates generally to implantable cardiac devices and, more specifically, to processing signal data from a sensor to conserve storage space in the implant while maintaining a low computational power requirement.

BACKGROUND

Implantable cardiac devices ("ICDs") such as pacemakers, defibrillators or implantable cardiac monitoring devices may be used in the treatment of patients who have impaired cardiac function. For example, some ICDs may stimulate a patient's heart to maintain regular contractions of the heart thereby promoting blood circulation within the patient. Such stimulation may be prescribed when the patient's heart does not function normally due to, for example, a genetic or acquired condition.

In a healthy heart, contractions occur first in the muscles associated with the atrium chambers of the heart, followed by contractions in the muscles associated with the larger ventricle chambers of the heart. In this way, the atria assist in the filling of the ventricle chambers with blood returning from the veins. This enables the ventricles to more efficiently pump blood to the arteries.

Given the interaction of these chambers, efficient operation of the heart is predicated on each of the chambers operating in a proper timing sequence and having contractions that pump a sufficient amount of blood from the chamber. For example, during contraction the right atrium chamber should pump enough blood to effectively "fill" the right ventricle chamber. Moreover, this should occur immediately before the right ventricle begins to contract. In this way, the heart may efficiently pump blood on a repetitive basis.

A healthy heart repetitively contracts in the above described manner in response to the generation and conduction of electrical signals in the heart. These electrical signals are generated in and conducted through the heart during every beat of the heart.

Under certain circumstances, an ICD may compensate for abnormal operation of a heart by pacing (e.g., stimulating) one or more of the atria and/or ventricles. To stimulate the heart, a typical ICD generates a series of electrical signals which are applied to the heart via one or more electrodes implanted in the heart (e.g., in ventricular or atrial chambers). These electrical signals cause the heart to contract in much the same way as the native electrical signals discussed above cause the heart to contract.

To provide appropriate timing for the generation of electrical signals, conventional ICDs may sense signals in the heart. For example, an ICD may sense electrical signals in the atria to detect when the atria are being activated. The ICD may then delay a prescribed period of time after which it senses electrical signals in the ventricles to determine whether to apply a stimulus to the ventricles. In this way, the ICD may stimulate the ventricles at the appropriate time in an attempt to maintain efficient operation of the heart.

The signals from the sensors in the heart are collected in the ICD to be analyzed to determine when a stimulus should be generated or other action taken. The data received from the sensors is stored as a time series of data. The time series includes a set of time indicators and a paired set of data samples. The time indicators record a relative or absolute time that a corresponding data sample was taken by a sensor. Each data sample includes a value that measures a signal, such as an amplitude of the signal captured by the sensors, at the indicated time. This time series data is analyzed by, for example, morphology detection algorithms and/or arrhythmia detection algorithms to identify cardiac activity (e.g., P-waves corresponding to atrial activity, R-waves corresponding to ventricular activity, and their origin, etc.). Based on the timing or absence of cardiac activity, the ICD may determine the timing for the application of electrical stimulation pulses to the heart.

Storing the time series data may require significant storage space and analyzing the data may be computationally intensive. As a result, current ICDs may limit the resolution and quality of the analysis of the data. In practice only a small subset of data may be stored and analyzed due to the limitations of the battery power of the ICD on computation and the space limitations on the size of memory in the ICD.

SUMMARY

Illustrative embodiments relate to a system and method for processing and storing signal information in an implantable cardiac device. The signal information may be reduced to a set of key elements that represent the signal in place of a time series of data representing the signal.

In some embodiments sensed cardiac signals initially represented as time series data are processed to generate key elements. For example, an analog sensed signal may be sampled by an analog to digital converter to generate the time series data. This data may thus define sensed cardiac signals such as P-waves, R-waves, etc.

The time series data may then be processed to generate key elements. In general, the key elements may consist of a set of information about the signal that is necessary and sufficient to represent and reconstruct the signal to a desired accuracy. Thus, information associated with a portion of the time series points may be discarded. For example, in some embodiments the key elements may indicate the beginning of a wave, a peak of the wave, an end of the wave, etc.

In some embodiments the key elements may sufficiently define the cardiac signals yet require less data memory storage than the corresponding time series data. Thus, in some embodiments these key elements may be stored in the implantable cardiac device instead of the time-series representations.

In some embodiments the key elements are processed to identify cardiac activity associated with the key elements. For example, the key elements may correspond to a P-wave, an R-wave, fibrillation or other cardiac activity. Processing of the key elements may therefore involve processing the key elements to determine when a given cardiac event has occurred.

In some embodiments processing of the key elements may be more efficient than processing of the corresponding time series data. For example, a morphology comparison of key elements with a key element template (e.g., of a P-wave) may involve less computation than a morphology comparison of a times series representation (e.g., of the P-wave) with a time series template.

In some embodiments a key element may include signal parameters relating to, for example, timing, amplitude, amount of change in slope and direction in change of slope. One or more of these parameters may then be used during key element processing (e.g., morphology matching).

In one embodiment, generation of key elements by the algorithm is done after pre-filtering and denoising techniques remove high frequency noise from the signal. As the signal elements are being generated by the algorithm, each element is evaluated; and only those elements with significant change in slope from the preceding element are kept as key elements. Key element signal representation is then used for any further processing or storage in place of the original time-series version of the signal.

For example, in one embodiment when IEGM storage is triggered, the key elements are stored in place of the original signal. Thus, when an MD algorithm or other algorithm is enabled the key elements of the cardiac signal during normal sinus as generated by the algorithm may be stored in memory in place of the time-series representation of the template. Also, during SVT discrimination and morphology scoring, a regular cross correlation or match filtering technique may be performed between key elements associated with the real time IEGM and the key elements associated with the stored template. Any one or a combination of key element parameters may be used in morphology match filtering to generate a percentage match score.

In one embodiment an implantable cardiac device includes a key element generator unit that processes a real-time stream of filtered or raw data from a buffer. The unit continually monitors two sliding windows at any given point in time $t_i$. Each window may be of length N+1. For example, one window may be a sliding window of length N+1, ending at time $t_i$, i.e., from $t_{i-N}$ to $t_i$. The other window may be a sliding window of length N+1, starting at $t_i$. The slope of best linear fit to each window may then be continually computed. When the difference between the slope of the line defined for the first window is significantly different from the slope of the line defined for the second window by at least a predetermined amount, the data point at time $t_i$ is considered a key element point. Thus, information associated with the point such as amplitude, timing, amount and direction of change in slope at that point may be stored as the parameters of that key element.

In one embodiment the unit continually monitors the first and second derivative of the real-time IEGM. When the absolute value of the first or second derivative of the signal is greater than a predefined threshold, the algorithm may generate a key element at that point. For example, the algorithm may store the amplitude and timing of that point from the original IEGM, and the amplitude and direction of the 2nd derivative value at that point. Alternatively, the algorithm may also store the slope (1st derivative) of the signal at that point, or the maximum slope of sliding average window around that point.

BRIEF DESCRIPTION OF THE DRAWINGS

Embodiments of the invention are illustrated by way of example and not by way of limitation in the figures of the accompanying drawings in which like references indicate similar elements. It should be noted that references to "an" or "one" embodiment in this discussion are not necessarily to the same embodiment, and such references mean at least one.

Figure 1:
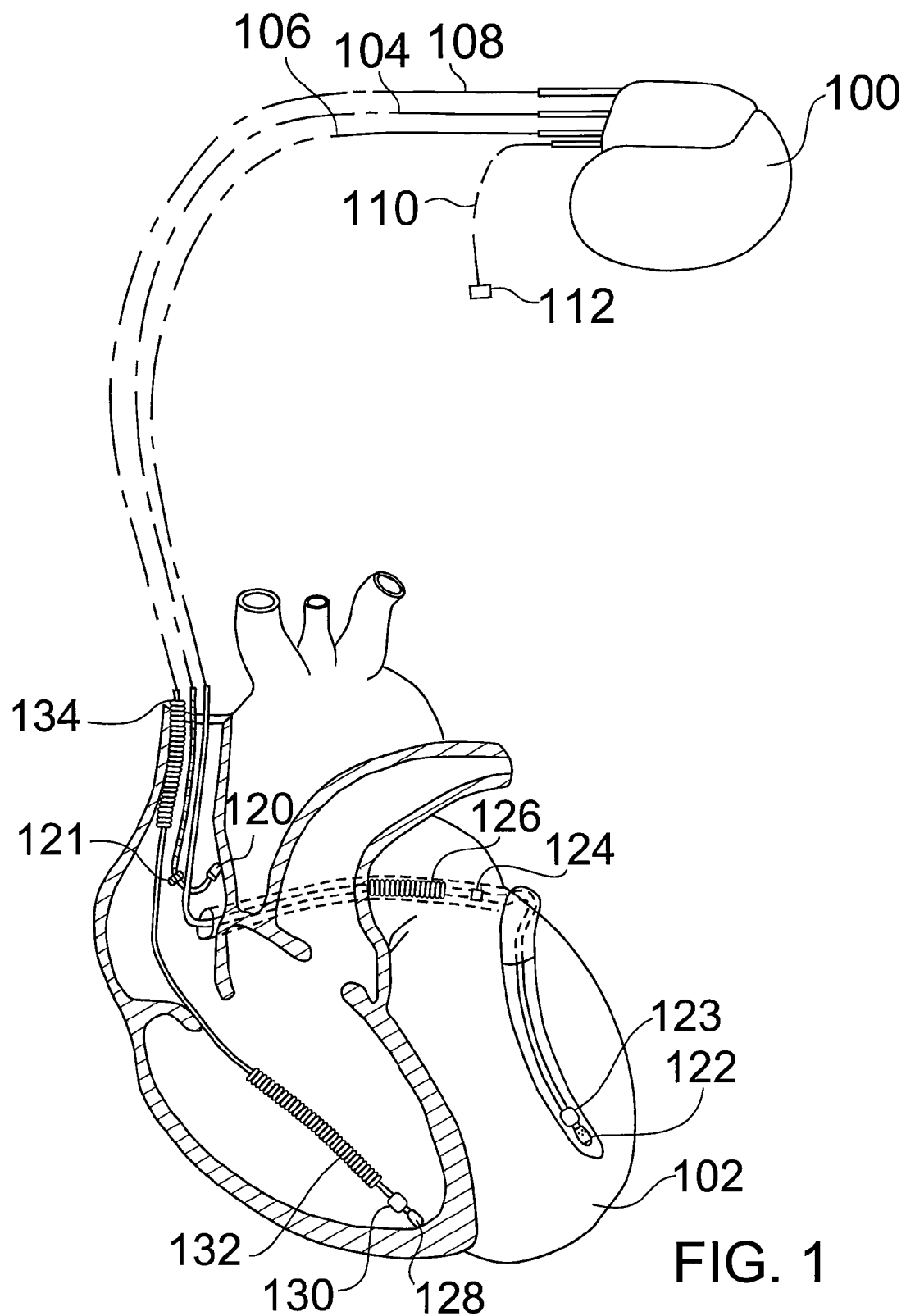
FIG. 1 is a simplified diagram of one embodiment of an implantable stimulation device in electrical communication with at least three leads implanted in a patient's heart for delivering multi-chamber stimulation and shock therapy in accordance with the invention.

In accordance with common practice, the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals denote like features throughout the specification and figures.

DETAILED DESCRIPTION

The invention is described below, with reference to detailed illustrative embodiments. It will be apparent that the invention may be embodied in a wide variety of forms, some of which may be quite different from those of the disclosed embodiments. Consequently, the specific structural and functional details disclosed herein are merely representative and do not limit the scope of the invention.

The following description sets forth but one exemplary stimulation device that is capable of being used in connection with the various embodiments of the invention that are described below. It is to be appreciated and understood that other stimulation devices, including those that are not necessarily implantable, can be used and that the description below is given, in its specific context, to assist the reader in understanding, with more clarity, the inventive embodiments described herein.

FIG. 1 is a simplified diagram of one embodiment of an exemplary stimulation device 100 in electrical communication with a patient's heart 102 by way of three leads 104, 106, and 108, suitable for delivering multi-chamber stimulation and shock therapy. To sense atrial cardiac signals and to provide right atrial chamber stimulation therapy, stimulation device 100 is coupled to an implantable right atrial lead 104 having, for example, an atrial tip electrode 120, which typically is implanted in the patient's right atrial appendage or septum. The right atrial lead 104 may have an optional atrial ring electrode 121.

To sense left atrial and ventricular cardiac signals and to provide left chamber pacing therapy, stimulation device 100 is coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using, for example, a left ventricular tip electrode 122, left ventricular ring electrode 123, left atrial pacing therapy using, for example, a left atrial ring electrode 124, and shocking therapy using, for example, a left atrial coil electrode 126 (or other electrode capable of delivering a shock). For a complete description of a coronary sinus lead, the reader is directed to U.S. Pat. No. 5,466,254, "Coronary Sinus Lead with Atrial Sensing Capability" (Helland), which is incorporated herein by reference.

Stimulation device 100 is also shown in electrical communication with the patient's heart 102 by way of an implantable right ventricular lead 108 having, in this implementation, a right ventricular tip electrode 128, a right ventricular ring electrode 130, a right ventricular (RV) coil electrode 132 (or other electrode capable of delivering a shock), and superior vena cava (SVC) coil electrode 134 (or other electrode capable of delivering a shock). Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle.

In some embodiments, the stimulation device 100 may receive signals from one or more other leads (e.g., lead(s) 110) and sensors (e.g., sensor(s) 112). These leads and sensors may be implanted in the heart or at other locations in a patient. These leads and sensors may be used to sense a variety of signals including, for example, pressure signals, impedance signals, respiration signals, pulse oximetry signals, SVO2 signals, accelerometer signals, etc.

Figure 2:
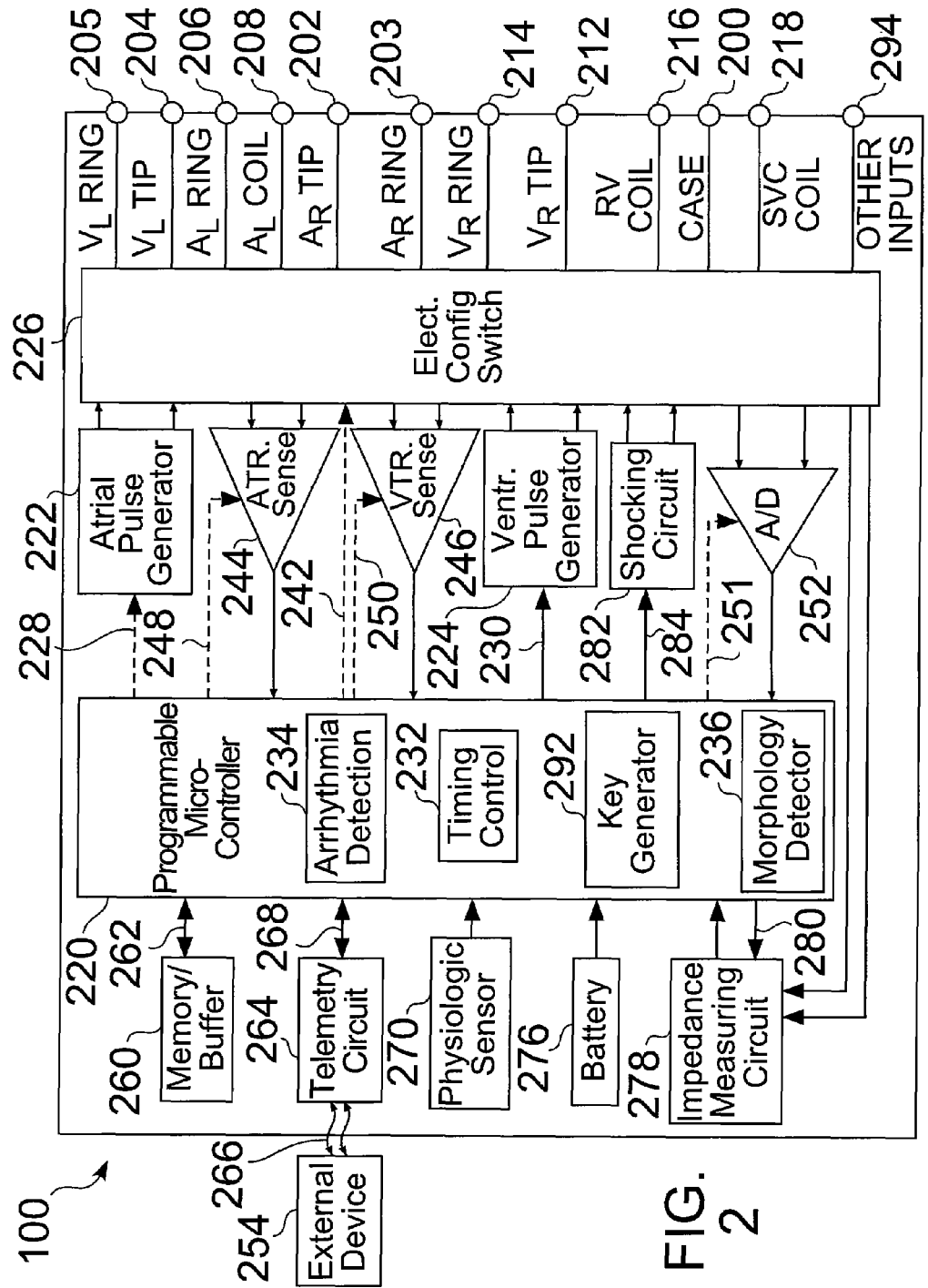
FIG. 2 is a simplified functional block diagram of one embodiment of a multi-chamber implantable stimulation device constructed in accordance with the invention, illustrating basic elements that are configured to provide cardioversion, defibrillation or pacing stimulation or any combination thereof.

FIG. 2 is a simplified diagram depicting various components of one embodiment of the stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

The housing 200 for stimulation device 100 is often referred to as the "can", "case" or "case electrode", and may be programmably selected to act as the return electrode for all "unipolar" modes. The housing 200 may further be used as a return electrode alone or in combination with one or more of the coil electrodes 126, 132 and 134 for shocking purposes. The housing further includes a connector (not shown) having a plurality of terminals 202, 203, 204, 205, 206, 208, 212, 214, 216, and 218 (shown schematically and, for convenience, the names of the electrodes to which they are connected are shown next to the terminals).

To achieve right atrial sensing and pacing, the connector includes, for example, a right atrial tip terminal (AR TIP) 202 adapted for connection to the atrial tip electrode 120. A right atrial ring terminal (AR RING) 203 may also be included adapted for connection to the atrial ring electrode 121. To achieve left chamber sensing, pacing, and shocking, the connector includes, for example, a left ventricular tip terminal (VL TIP) 204, left ventricular ring terminal (VL RING) 205, a left atrial ring terminal (AL RING) 206, and a left atrial shocking terminal (AL COIL) 208, which are adapted for connection to the left ventricular tip electrode 122, the left atrial ring electrode 124, and the left atrial coil electrode 126, respectively.

To support right chamber sensing, pacing, and shocking, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

In some embodiments, the connector may include one or more terminals (e.g., terminal 294) for receiving signals from other input leads and sensors. For example, the terminal(s) 294 may be used for receiving signals such a those discussed above in conjunction with lead(s) 110 and sensor(s) 112.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, and the other lead(s) 110 through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from one or more of the sensing circuits 244 and 246, the data acquisition system 252, the data memory 260 and other components in the device 200 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals or other signals (e.g., from terminal(s) 292) also may be applied to inputs of an analog-to-digital (A/D) data acquisition system 252. The data acquisition system 252 is configured (e.g., via signal line 251) to acquire intracardiac electrogram (IEGM) signals, convert the raw analog data into a digital signal and, in some embodiments, store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252 or other components), which data may then be used for subsequent analysis to guide the programming of the device.

The storage and processing of incoming data may be carried out by a key generator 292 and associated circuitry. The key generator 292 may process data received from one or more of the atrial channel (e.g., via sense circuit 244), the ventricular channel (e.g., via sense circuit 246), the data acquisition system 252 or any other source of input for the stimulation device 100. The key generator 292 may process the incoming data or signal to identify key data to be stored in, for example, the data memory 260. In some embodiments key data are data samples and information that allow for the reconstruction of the other data that is dropped. For example, a key data for an IEGM may be a point in a signal or sample of a signal that coincides with a change in slope of the IEGM signal. Data related to this point is stored including, for example, one or more of time, amplitude, amount of change in slope, direction of change in slope or other information about the point identified as a key data element. This key data may be utilized by other components such as the morphology detector 236, arrhythmia detection component 234, timing control circuit 232, physiological sensor 270 or any other component of the stimulation device 100 or any external device 254 in place of time series data or other representations of the original cardiac signals.

Advantageously, the operating parameters of the implantable stimulation device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiological sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses. While shown as being included within the stimulation device 100, it is to be understood that the physiological sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors to help detect movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected. The stimulation device 100 may employ lithium, nickel-cadmium, or similar battery technology.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that an external device 254 is in place to receive or transmit data to the microcontroller 220 through the telemetry circuit 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 to 2.0 J), moderate (e.g., 2.5 J to 10 J), or high energy (e.g., 11 J to 40 J), as controlled by the microcontroller 220. Such shocking pulses are applied to the patient's heart 102 through, for example, two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, and/or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Figure 3A:
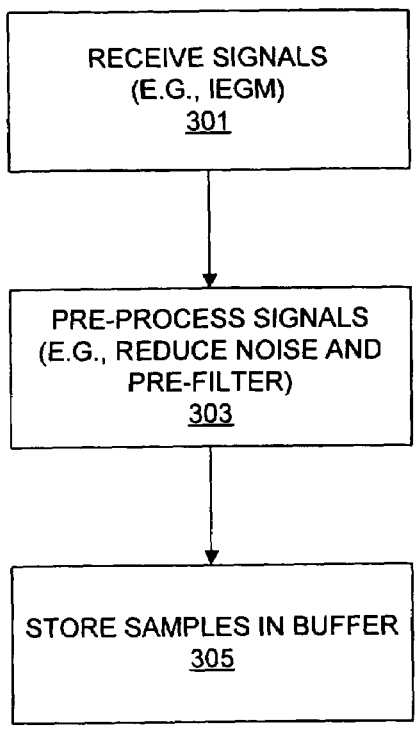
FIG. 3A is a simplified flow chart of one embodiment of a process to buffer received signal data.

FIG. 3A is a flowchart of one embodiment of a process for processing received signals and storing the received signals. This process may be executed by, for example, the key generator circuit, another component of the microcontroller, the data acquisition system or another component of the implantable device. In one embodiment these or other components may cooperate to perform the desired operations.

A signal or similar data (referred to hereafter as a signal for convenience) is received by the implantable device through the data acquisition system, the atrial sense circuit, the ventricular sense circuit or another processing circuit (block 301). The received signals may be obtained, for example, by sensing signals associated with cardiac electrical activity, pressure, respiration, pulse oximetry, SVO2, impedance, acceleration, etc. For convenience, one or more of these components may be referred to herein as an "input processing circuit."

The input processing circuit may alter an incoming signal to, for example, improve its quality. In one embodiment the microcontroller in combination with the input processing circuit may adjust the gain of the signal, bandpass filter the signal or modify similar aspects of the incoming signal. The adjustments to the incoming signal may be aimed at reducing the noise on the incoming line as well as filtering the signal to remove artifacts and isolate or improve the aspects of the signal that are needed (block 303).

In one embodiment, the data may also be converted from an analog signal to a digital representation of the signal by the input processing circuit, an analog to digital converter or similar device. In one embodiment, the analog to digital conversion may take place at the sensor or at another location in the system. Initially, the data may be in the form of a series of samples over time, that is, a times series of data, or a similar format of data. In one embodiment, the data may be received at a range of sample rates. For example, an IEGM signal may be received with a sample rate of 2 ms or larger sample rate. The sample rate indicates the overall resolution or quality of the incoming signal or data.

After the data is processed by the input processing circuit, etc., the processed data may be used to generate key elements. In one embodiment the processing of key elements may be performed in real-time as the processed data is generated.

In one embodiment, as represented by block 305, the processed data is stored as a set of samples in a buffer. In this way the data may be processed at a later time, if desired. The buffer may have any size. In one embodiment, the buffer may have a pair of 25 or 50 ms windows. In another embodiment, the buffer may be conceptualized as a single sliding window. As each additional sample or data point is stored in the buffer an older sample may be overwritten or shifted out of the buffer if the buffer is full. In one embodiment, the buffer may be a part of the working memory or similar component of the microcontroller. In another embodiment, the buffer may be a separate memory device or part of the standard memory device (e.g., memory 206) of the implantable device.

Figure 3B:
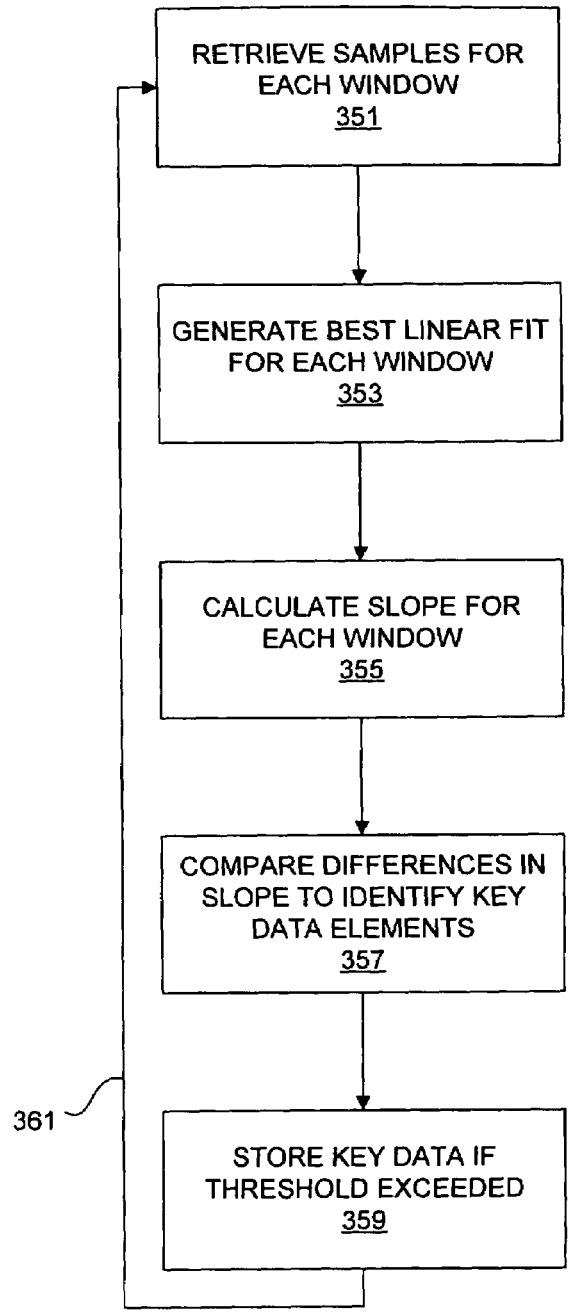
FIG. 3B is a simplified flow chart of one embodiment of a process performed by a key generator circuit.
Figure 4:
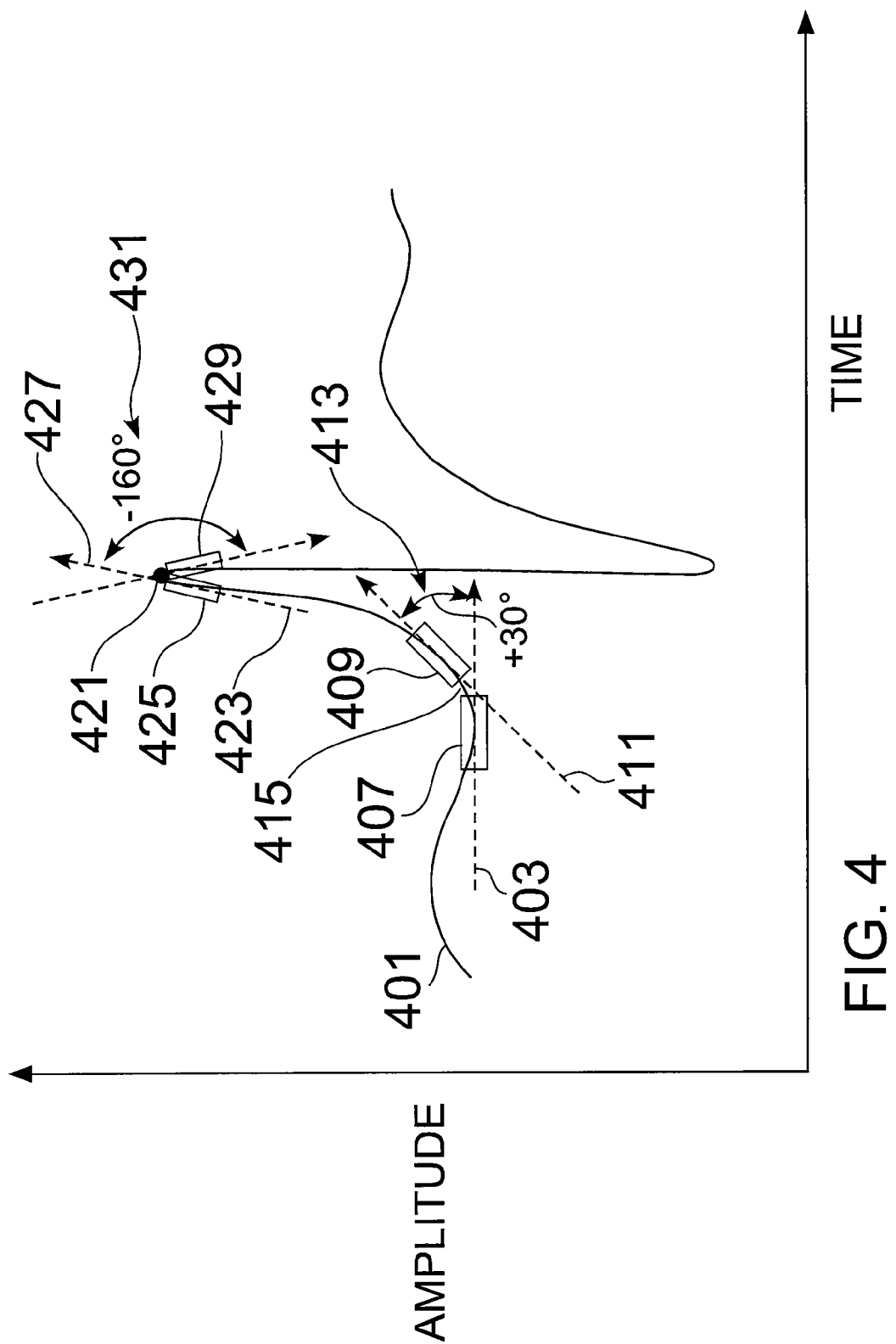
FIG. 4 is a simplified diagram depicting one example embodiment of a PQRST signal.
Figure 5:
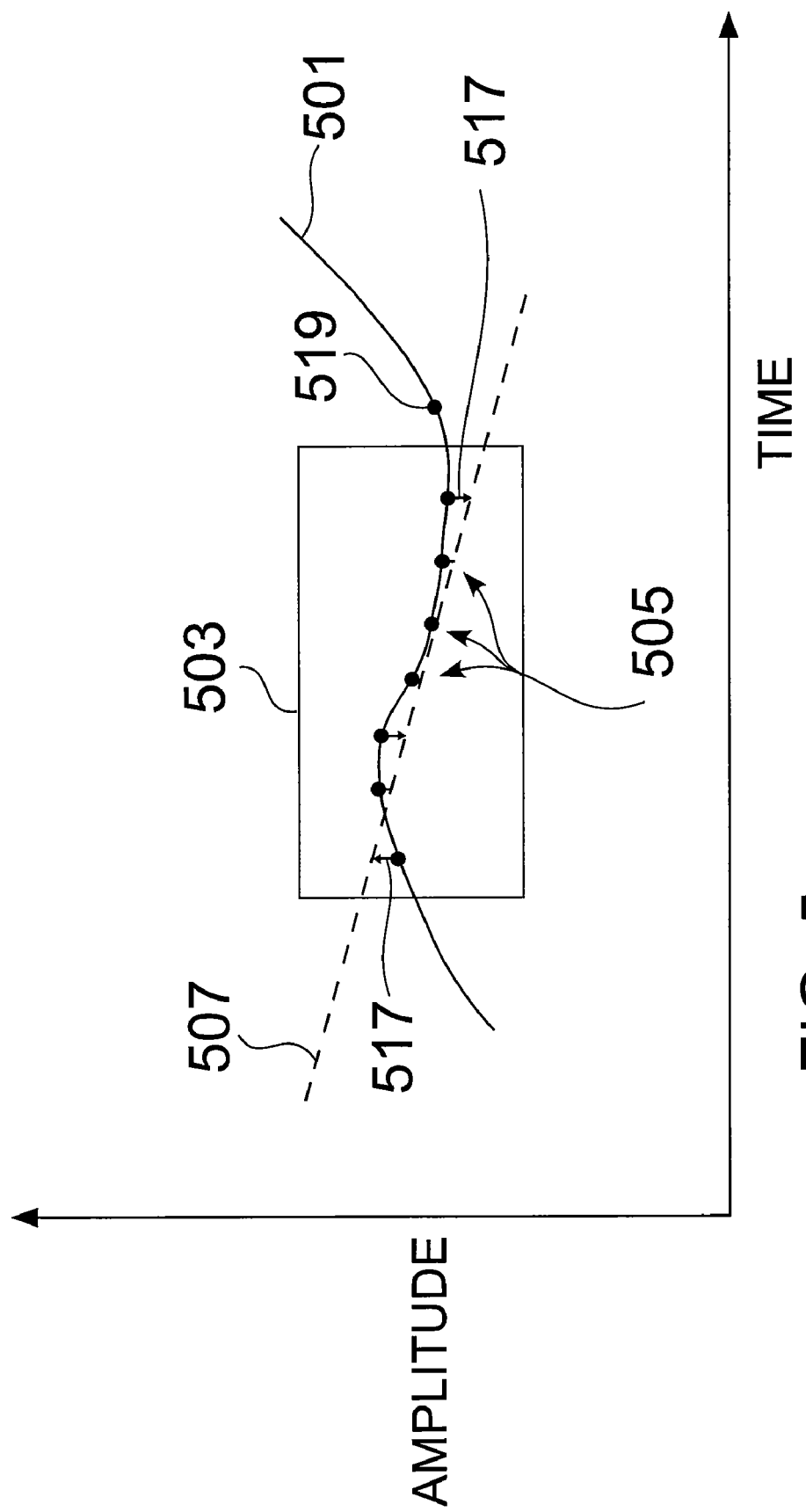
FIG. 5 is a simplified diagram depicting one example embodiment of a determination of a linear fit for a set of data.

FIG. 3B is a diagram of one embodiment of a process for processing data into a set of key elements. Reference is also made to FIGS. 4 and 5 which are examples of a signal that is being processed and a representation of a best linear fit process, respectively. In one embodiment, this process begins as the key generator accesses the buffer to analyze the data stored in each window (block 351). The key generator may access the data in place or retrieve data from the buffer to be worked on, dependent on the location of the buffer. In one embodiment, the data in one window of the buffer represents a set of data points that precedes, in time, the data point to be analyzed. The data in the second window represents a set of data points that are subsequent, in time, to the data point to be analyzed. For example, referring to FIG. 4, the key generator may analyze a data sample at a point 415 in signal 401. The first window 407 (graphically represented as a box around a set of points in a signal) contains a set of points preceding the point 415 and the second window 409 (also graphically represented as a box) contains a set of points after the point 415.

In one embodiment, after the data in each window is accessed, a best linear fit is determined for the data in each window (block 535). Any linear fit algorithm or process may be utilized to determine the linear fit for each set of data. In general, a linear fit algorithm attempts to plot a line through a set of points while attempting to minimize the distance between the line and each point in the data set.

FIG. 5 shows a graphical example where a linear fit has been calculated for a set of points 505 associated with a signal 501 that fall within a window 503. The linear fit algorithm calculates a slope and placement of a line 507 through the set of points 505 that minimizes the distances (as represented by arrows 517) between the points 505 and the line 507. The algorithm may utilize the entire set of data points 505 in the window 503 related to the signal 501 or a subset of the data points 505. If the average distance between the points and the line is too high, or if the distance to outlying points is too great or similar error calculations indicate that the line 507 is not sufficiently accurate in its placement, then the number of data points utilized may be reduced (e.g., the window size is reduced) and the best linear fit recalculated. In one example embodiment, the error calculation may be based on the distance from the analyzed point to the line. In one embodiment, if an error for the line fit is too high, then points further back in time or furthest away from a point 519 to be analyzed may be dropped first and the best linear fit recalculated. The method of dropping points and the tolerance for error may be dependent on the best linear fit algorithm selected and the programmable settings of the implantable device. In one embodiment, the analyzed point 519 may be included in each linear fit calculation. In another embodiment, it may be excluded.

In one embodiment, after the best linear fit is calculated for each window, the slope of each line may be calculated (block 355). The differences between the slopes of the lines for each window may then be calculated. Referring to FIG. 4, in this example the slope of the line 403 for the first window 407 has a difference 413 of thirty degrees from the slope of the line 411 for the second window 409.

Next, the difference between the slopes of the lines for each window may be compared to, for example, a threshold value (block 357). The threshold value may be a fixed value stored in the memory or in the microcontroller of the implantable device. The threshold value may be programmable or preset. In one embodiment, the difference value 413 may be accumulated over time to prevent continuous small changes of slope in one direction from going undetected. In one embodiment, the threshold value may be between 1 and 30 degrees. If the difference 413 exceeds the threshold value then the data associated with the point 415 being analyzed may be defined as key data. The key data is discussed in more detail below.

In another embodiment, the best linear fit and slope of the line may not be calculated to identify a key data element. Instead, a first derivative may be calculated for the point being analyzed in the signal. The derivative may be based on an average sliding window of data points in the buffer preceding and subsequent to an analyzed point. If the absolute value of the first derivative exceeds a threshold value then key element data is stored for the associated point or sample. In a further embodiment, the second derivative may also be calculated and if it exceeds a threshold value, then storage of the key element data for the point may be triggered. The second derivative may also be based on a sliding average window of data in the buffer. Separate threshold values may be used for the first and second derivatives. The threshold values may be programmable or preset.

It should be appreciated that a variety of information (e.g., parameters) may be associated with a key data element. For example, 'key data' may include time (in either a relative or absolute format), amplitude, amount of change in slope, direction of change in slope, derivatives of slopes, second derivatives, maximum slope of a sliding average window around the key element point, angular parameters or similar information.

As represented by block 359, the key data may be stored in a data memory for subsequent processing. Thus, storage of key data may include storing one or more of the slope of the signal at the analyzed point, the maximum slope of a sliding average window around the point, the second derivative and other data such as that mentioned above. The type and amount of key data stored may be programmable. The key data may be stored in the primary memory of the device. In one embodiment, additional criteria may be used to determine if the key data is stored or maintained. Additional criteria may include a change in time from the last stored key data, a change in amplitude between adjacent stored data, a change in difference in slope between adjacent data, a change in slope or second derivative or similar criteria. These additional criteria may be used to limit the storage of redundant key data. This set of additional criteria may be programmable or preset. In another embodiment, a separate process analyzes stored key data based on these criteria and discards or overwrites any redundant key data.

In one embodiment, as represented by the line 361, after the key data is stored the key generator continues to process the time series data. For example, in one embodiment the process advances to the next point in the signal and retrieves or accesses the window data necessary to analyze the next point (block 351). If the difference value does not exceed the threshold value then no data is stored related to the analyzed point.

The processes of FIGS. 3A and/or 3B may be continuous and executed in real-time to provide the implantable device with constant real time data about heart sensor or other sensor information received from sensors or other input sources. For example, the key element data may be generated and processed on a beat-by-beat basis, a breath-by-breath basis, etc.

FIG. 4 depicts a key element process at another point 421. Here, a line 423 (e.g., from a best fit algorithms) is defined for a set of points within a preceding window 425. In addition, a line 427 is defined for a set of points within a following window 429. In this example, the difference 431 between the slopes for the lines 423 and 427 is −160 degrees.

In one embodiment, the key generator may advance to analyze a point or sample of data that is not the immediately next point or sample. For example, to reduce the amount of processing, the key generator may analyze fewer than all of the sampled points.

The key data described herein may be used to represent an incoming signal. For example, by identifying significant points in the signal (e.g., significant changes in slope, etc.), the key data may be used to identify specific cardiac events such as P-waves, R-waves, tachycardia, the origin of such events, etc. The key data also may be used to identify and/or characterize other events such as blood pressure, respiration rate, heart beat rate, etc. As an example, in a received cardiac pressure signal key elements may be defined at the systolic point and the diastolic point.

Moreover, the signal may be represented using less data than may be required to represent the signal using conventional time series data. For example, the number of key elements used to represent a signal may be less than the original number of data points that were sampled from the signal. The requirement for less information may, in turn, result in the need for less data memory for storing the representation of the signal and may reduce the computational complexity of any operations that process the signal representation.

Accordingly, the key data may be utilized by other components and algorithms in the implantable device such as the arrhythmia detector, morphology detector, timing control or other components. As mentioned above, the stored key data may enable such components of the stimulator to analyze the signal in a less computationally complex manner and with less data being stored than through the use of traditional time series data. This may prolong the battery life of the stimulator and may allow additional and more complete analysis of data in the implantable device to be undertaken.

In general, any signal received or processed by the implantable device may be reduced to key data including an IEGM, other atrial sense signals, other ventricular sense signals and other signals handled by the stimulator. For example, a complete PQRST signal may be stored as key data. This system may be particularly effective in representing the PQRST signal because a known set of key elements can be expected to be detected that describe the PQRST signal accurately. That is, an IEGM may constitute a periodic signal with known features as opposed to a random signal. As a result, a set of key elements may be reliably and efficiently associated with the PQRST complex in the IEGM. In one embodiment, this technique may reduce a set of over 800 time series data samples to a set of less than 50 key data elements.

In one embodiment the key data may be utilized by a cross-correlation algorithm, a morphology discrimination (MD) algorithm, etc., that maintains a template of an IEGM or similar signal as a model signal. An example of operations that may be associated with an algorithm such as this is described in FIG. 6.

Figure 6A:
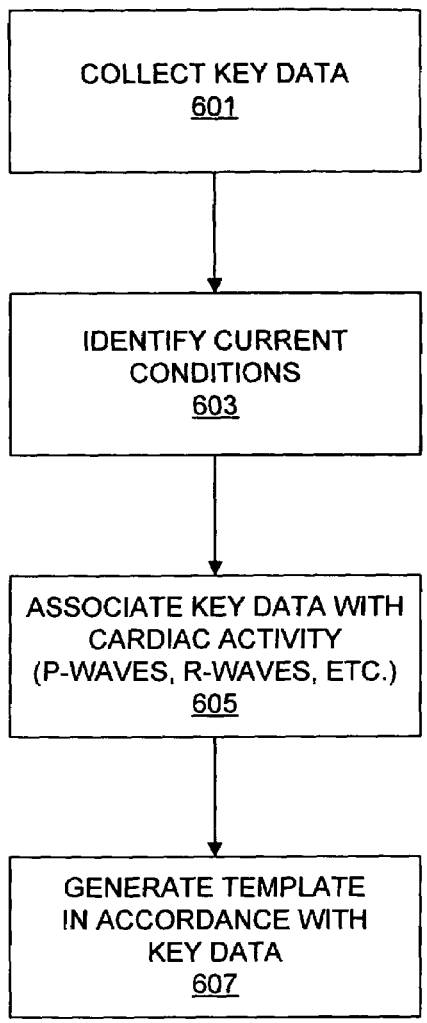
FIG. 6A is a simplified flow chart of one embodiment of a process for generating key data templates.

As represented by FIG. 6A, the template may be stored as a set of key data. The template may be a static template or a dynamically updated template. Initially, as represented by block 601, the device may collect key data over time. When the key data is being collected, the device also may identify current conditions (e.g., whether a patient has a normal sinus rhythm or an abnormal rhythm, the activity level of the patient, etc.) to provide a proper frame of reference for the collected data.

As represented by block 605, the key data may be analyzed to identify specific cardiac activity that is associated with specific sets of key data. In one embodiment this may involve using other tools (e.g., an electrocardiogram analysis tool) to verify that a given cardiac signal (e.g., p-wave) is currently being sensed so that a given set of key data is identified as being associated with that specific cardiac signal (e.g., p-wave).

As represented by block 607, one or more templates may thus be defined in accordance with the key data. For example, one template containing a set of key data may be used for p-wave matching. Another template containing another set of key data may be used for r-wave matching, etc. In one embodiment the templates may be adjusted over time to ensure that they accurately correspond to the cardiac signals sensed within the patient. The resulting templates may then be stored in a data memory in the device.

An algorithm such as the MD algorithm may use the key data to determine what type of specific cardiac activity (e.g., p-waves, r-waves, ventricular or atrial arrhythmias) has occurred to provide the appropriate therapy (e.g., stimulation, shocks, etc.) for the patient. Due to the simplified nature of the stored key data, in one embodiment a real cross-correlation of values may be executed, whereas the traditional approach using time series data may be too complex to perform true cross-correlation.

Figure 6B:
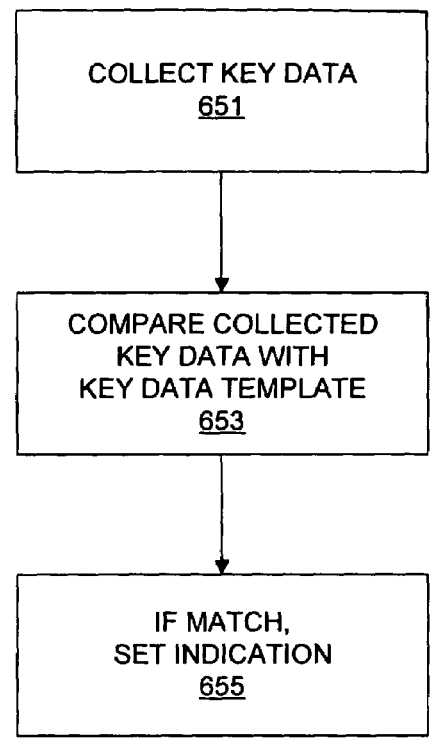
FIG. 6B is a simplified flow chart of one embodiment of a process for identifying cardiac activity using key data and key data templates.

As represented at block 651 in FIG. 6B, the device may collect key data in, for example, real-time. At block 653 the collected key data may be compared with one or more stored key data templates. A match between the collected key data and the template may be indicated, for example, when the collected data falls within a range of values associated with the template. If there is a match, the device may then set a corresponding indication (e.g., p-wave detect, r-wave detect, arrhythmia detect, etc.).

It should be appreciated that other algorithms may utilize the key data. For example, such algorithms may include Schemia detection, T segment elevation for hypoglycemia detection, QRS width detection, T wave Alternans and other algorithms that analyze an IEGM signal or other signal handled by the implantable device. The key data can also be easily and compactly utilized to track and detect intervals between signals.

It should be appreciated that the various components and techniques described herein may be incorporated in an apparatus (e.g., an implantable device, a lead, etc.) independently of the other components and techniques. For example, an apparatus incorporating the teachings herein may include various combinations of these components and techniques. Thus, not all of the components and techniques described herein may be employed in every such apparatus.

Different embodiments of the implantable device may include a variety of hardware and software processing components. In some embodiments of the invention, hardware components such as controllers, state machines and/or logic are used in a system constructed in accordance with the invention. In some embodiments, code such as software or firmware executing on one or more processing devices may be used to implement one or more of the described operations.

The components and functions described herein may be connected/coupled in many different ways. The manner in which this is done may depend, in part, on whether and how the components are separated from the other components. In some embodiments some of the connections/couplings represented by the lead lines in the drawings may be in an integrated circuit, on a circuit board or implemented as discrete wires.

The signals discussed herein may take several forms. For example, in some embodiments a signal may be an electrical signal transmitted over a wire while other signals may consist of wireless signals transmitted trough space. In addition, a group of signals may be collectively referred to as a signal herein. The signals discussed above also may take the form of data. For example, in some embodiments an application program may send a signal to another application program. Such a signal may be stored in a data memory.

In summary, the invention described herein generally relates to an improved system and method for processing and storing data in an implantable cardiac apparatus such as an ICD. While certain exemplary embodiments have been described above in detail and shown in the accompanying drawings, it is to be understood that such embodiments are merely illustrative of and not restrictive of the broad invention. In particular, it should be recognized that the teachings of the invention apply to a wide variety of systems and processes. It will thus be recognized that various modifications may be made to the illustrated and other embodiments of the invention described above, without departing from the broad inventive scope thereof. For example, a variety of techniques including techniques other than those specifically disclosed above may be used to identify important points (e.g., key elements) in a received signal. A variety of information including information other than that specifically disclosed above may be associated with the important points. A variety of techniques for comparing key elements including techniques other than those specifically disclosed above may be used to identify an incoming signal. Key element data may be used in operations other than those specifically disclosed above. In view of the above it will be understood that the invention is not limited to the particular embodiments or arrangements disclosed, but is rather intended to cover any changes, adaptations or modifications which are within the scope and spirit of the invention as defined by the appended claims.

What is claimed is:

1. A method of representing a sensed signal comprising:
   receiving, in an implantable cardiac device, a signal from a sensor;
   defining a plurality of points associated with the received signal;
   identifying points from the plurality of points, wherein each of the identified points are associated with a change in slope of the received signal that is greater than at least one threshold;
   storing data associated with the identified points; and
   defining a plurality of sliding windows for generating slope information associated with the signal, wherein a first one of the sliding windows comprises points preceding a point of interest and a second one of the sliding windows comprises points following the point of interest.

2. The method of claim 1 comprising comparing the difference between slope information generated for each sliding window with the threshold to identify the points.

3. The method of claim 1 comprising:
   associating a subset of the plurality of points with each sliding window;
   generating a best linear fit for each subset of the points for each sliding window;
   calculating a difference in slope between each best linear fit; and
   comparing the difference with the at least one threshold to provide the identified points.

4. The method of claim 1 wherein the data defines at least one of amplitude, time, amount of change in slope and direction in change of slope.

5. The method of claim 1 wherein the defining a plurality of points comprises sampling the received signal to generate sampled signals.

6. The method of claim 5 comprising storing the sampled signals in a buffer.

7. The method of claim 1 wherein the received signal comprises one of an intracardiac electrogram signal, a pressure signal, a respiration signal, an impedance signal, a pulse oximetry signal, an SVO2 signal and an accelerometer signal.

8. A method of characterizing a sensed signal comprising:

receiving, in an implantable cardiac device, a first signal from a sensor;

defining a first plurality of points associated with the first received signal;

identifying a first set of points from the first plurality of points, wherein each of the identified points in the first set are associated with a change in slope of the first received signal that is greater than a first threshold;

defining a plurality of sliding windows for generating slope information associated with the first signal, wherein a first one of the sliding windows comprises points preceding a point of interest and a second one of the sliding windows comprises points following the point of interest;

comparing data associated with the first set of identified points with at least one template; and generating an indication when the first set of identified points match the at least one template.

9. The method of claim 8 wherein the at least one template comprises points that are each associated with a change in slope of a second received signal greater than a second threshold.

10. The method of claim 8 comprising generating the at least one template comprising:

receiving a second signal from the sensor;

defining a second plurality of points associated with the second received signal;

identifying a second set of points from the second plurality of points, wherein each of the identified points in the second set are associated with a change in slope of the second received signal that is greater than a second threshold; and associating data associated with the second set of identified points with the at least one template.

11. The method of claim 8 wherein the data defines at least one of amplitude, time, amount of change in slope and direction in change of slope.

* * * * *